United States Patent [19]

Jastrzebski et al.

[11] Patent Number: 4,498,772
[45] Date of Patent: Feb. 12, 1985

[54] METHOD TO DETERMINE THE CRYSTALLINE PROPERTIES OF AN INTERFACE OF TWO MATERIALS BY AN OPTICAL TECHNIQUE

[75] Inventors: Lubomir L. Jastrzebski, Plainsboro, N.J.; Jacek Lagowski, Wobum, Mass.

[73] Assignee: RCA Corporation, New York, N.Y.

[21] Appl. No.: 439,562

[22] Filed: Nov. 5, 1982

[51] Int. Cl.$^3$ .................. G01B 9/02; G01B 11/02
[52] U.S. Cl. .................. 356/357; 250/339; 356/361; 356/382
[58] Field of Search ............... 356/352, 357, 361, 382; 250/339

[56] References Cited

U.S. PATENT DOCUMENTS 4,352,016  9/1982  Duffy et al. ............... 250/358.1
4,352,017  9/1982  Duffy et al. ............... 250/358.1

OTHER PUBLICATIONS

Ruiz-Urbieta et al., "Methods for Determining Film Thickness and Optical Constants of Films and Substrates", *JOSA*, vol. 61, No. 3, pp. 351-359, 3/71.

Goodman, "Optical Interference Method for the Approximate Determination of Refractive Index and Thickness of a Transparent Layer", *Applied Optics*, vol. 17, No. 17, pp. 2779-2787, 9/1/78.

"Optical Properties of Thin Solid Films" by O. S. Heavens, 1965, Dover Publications, Inc., New York, pp. 57-59 and 156-158.

*Primary Examiner*—Davis L. Willis
*Assistant Examiner*—Matthew W. Koren
*Attorney, Agent, or Firm*—Birgit E. Morris; Donald S. Cohen; Joseph D. Lazar

[57] ABSTRACT

Crystalline quality of a semiconductor material at its interface with an insulator is optically evaluated by a reflected light beam scanned in wavelength. The refractive index of the material at or near the interface is determined by calculation from the measured values of reflectivity extrema and compared, if desired, to the bulk refractive index of the material. This index is an indicia of the crystalline quality at the interface.

4 Claims, 6 Drawing Figures

METHOD TO DETERMINE THE CRYSTALLINE PROPERTIES OF AN INTERFACE OF TWO MATERIALS BY AN OPTICAL TECHNIQUE

This invention relates to a method for determining the crystalline quality of the interface of two materials, and, more particularly, for determining the silicon-on-sapphire (SOS) interface by an optical technique.

BACKGROUND OF THE INVENTION

Silicon-on-sapphire (SOS) plays an important role as material especially suited for radiation-hard integrated circuits. The SOS technology has also been considered as a potential contributor to high performance very large scale integrated (VLSI) and very high scale integrated (VHSI) circuit applications. Recent work on SOS devices has clearly demonstrated a direct relationship between the crystalline perfection of SOS films and device parameters. It has also been shown that crystalline imperfections have a detrimental effect on electronic properties of SOS films, such as excess carrier lifetime, trapping centers, degree of amorphization and microscopic electrical inhomogeneities.

The pace of the optimization of the properties of materials in the heteroepitaxial silicon technology is closely related to the ability to characterize the quality of the deposits. The entire thickness of the film can be observed by cross-section transmission microscopy, but this method is laborious and time consuming, and therefore cannot serve as a rapid feed-back for material optimization efforts. UV reflectometry now serves as a rapid method to characterize the crystalline quality of the heteroepitaxial silicon surface most remote from the silicon/sapphire interface. See U.S. Pat. Nos. 4,352,016 and 4,352,017 issued on Sept. 22, 1982 to M. L. Duffy, et al. for a description of the use of U.V. reflectivity for determining the quality of silicon layers. No method is currently available, however, for the characterization of the crystalline nature of the silicon near or at the silicon/sapphire interface. Specific aspects of device performance (for instance, leakage current) are associated with the properties of the silicon near the sapphire interface. Such information is quite useful to the art.

SUMMARY OF THE INVENTION

According to the method of the present invention, the reflectivity of light from the surface of a layer of one material in the visible and near infrared spectrum is related to the crystalline quality of the layer of material, such as silicon, on a substrate of material of a different crystalline quality, such as sapphire.

The method comprises exposing the surface of a semiconductor material layer on an insulating material substrate to a wavelength scanned light beam to provide an oscillating reflection generated by interference reflections between the surface and the interface with the substrate; measuring the intensity of the reflections to obtain a series of wavelength related intensity signals; determining reflectivity extrema from the intensity signals; and determining from the extrema the refractive index of the semiconductor material at or near the interface.

DETAILED DESCRIPTION OF THE PREFERRED EMBODIMENT

Figure 1:
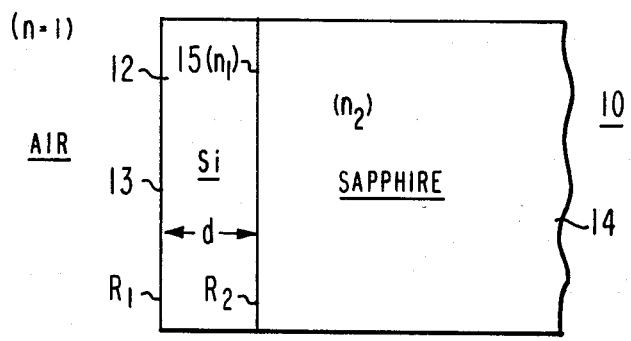
FIG. 1 is a schematic of a body of semiconductor material (SOS) illustrating the optical properties of the body.

A semiconductor body 10 useful in practicing the method of the invention is illustrated in FIG. 1. Body 10 is formed of an insulating substrate 14 upon which is deposited a layer of semiconductor material 12. While the invention can be practiced on any semiconductor material deposited on an insulator, the present embodiment will be described with reference to a semiconductor body 10 formed of a sapphire substrate 14 on which a layer 12 of silicon on the order of 0.5 to 1.0 micrometer is deposited. The refractive index of the sapphire is $n_2$. The refractive index for the bulk portion of the silicon film 12 is $n_0$. The refractive index for the ambient air is unity. The thickness d of the layer 12 is as illustrated in FIG. 1. The reflection coefficients $R_1$ and $R_2$, respectively, are related to the surface 13 of the layer 12 and the interface 15 of the layer 12 and substrate 14.

The refractive index at or near the interface 15 is $n_1$. The index $n_1$, as will be described, is different from the bulk index $n_0$. The determination of the index $n_1$ is a characterization of the crystalline quality of the interface as taught by the present specification.

We have discovered during the process of determining the index of refraction $n_1$ of material at or near the interface 15 of the layer surface 12 and the insulating body of sapphire 14, that there appeared unexpected differences between the experimental value of the refractive index $n_1$ and the value of the bulk index of refraction $n_0$ as known in the literature as obtained by separate measurements. From this, we speculated that the quality of the crystalline material of the semiconductor material at or near the interface was different from the quality of the bulk crystalline material. Nothing in the literature known to us indicates that there is a difference between the two indicies $n_0$ and $n_1$. Our speculation of this dissimilar relationship was confirmed based on further studies, as will be described, showing that there is no measurable difference in the bulk index $n_0$, whether the SOS was made from as-grown semiconductor kayers, heat-treated semiconductor layers or hydrogenated semiconductor layers. Surprisingly, however, we discovered that the value of $n_1$ is different in each of such layers. Our observations can be explained from our discovery that the interface region near the Si/Sapphire interface has different optical properties than the optical properties of the rest of the Si layer. This interfacial region is much thinner than the bulk film thickness, d. Accordingly, this thin interfacial region will not affect the bulk index of refraction $n_0$ but it will affect the reflection of the light ($R_2$) of the interface 15. The quality of the interface 15 is determined by comparing the index of refraction ($n_1$) in the interface region, i.e., at or near the interface, with the index of refraction ($n_0$) of the bulk portion of that material. The manner in which these index parameters $n_0$ and $n_1$ are determined will be explained in detail.

Monochromatic light is scanned in wavelengths to provide a substantially continuous beam of light varying in wavelength within a predetermined optical spectrum, for example, 0.5 to 1.0 micrometer. This wavelength-scanned light is used in the reflection measurements, to be discussed in greater detail, by illuminating the surface 13 of the semiconductor material 12 at close to normal incidence.

Figure 2:
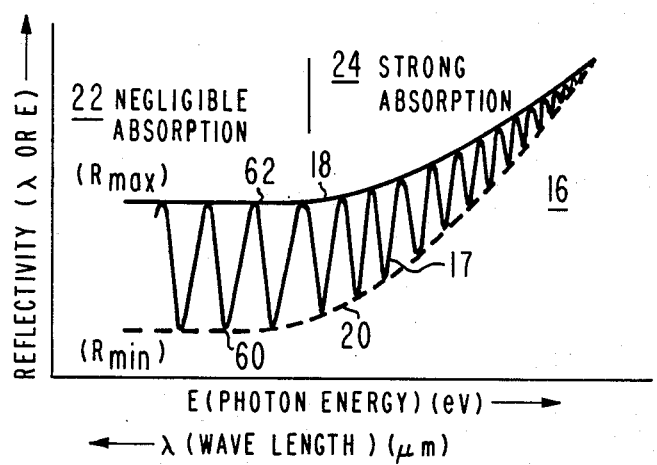
FIG. 2 is a plot of photon energy or wavelength versus reflectivity illustrating the reflectivity oscillations defining the extrema of reflections.

The intensity of reflected light as a function of photon energy or reciprocal wavelength is shown in FIG. 2 as curves 16. The reflectivity intensity signal 17 measured as a function of photon energy (E) in electron volts (eV) or wavelength ($\lambda$) in length of micrometers ($\mu$m), exhibits a sequence of interference maxima-minima within the envelopes 18 and 20 of the extrema, respectively. Accordingly, each point on envelope 18 is the maximum reflection ($R_{max}$) while the curve 20 represents the minimum reflection points ($R_{min}$). As will be further explained, the curves 16 of FIG. 2 indicate that in an energy region 22 of negligible absorption the reflectivity extrema are measurable, while in an energy region 24 of strong absorption, the extrema are not easily measured. In general, the energy or wavelength position of maxima-minima can be used to determine the value and energy dependence of the refractive index $n_0$ of the bulk semiconductor material in layer 12. In a low photon energy range, for example, $\alpha d \ll 1$, where $\alpha$ is the absorption coefficient of the silicon material in layer 12, and d is its thickness (FIG. 1), the reflectivity values of maxima and minima provide a measure of the reflection coefficient $R_1$ and $R_2$. In a higher photon energy range, the amplitude of reflectivity oscillations, as manifested by the envelope curves 18 and 20 of FIG. 2, decreases due to absorption, whereby the oscillations rapidly vanish when $\alpha d$ exceeds one. In the embodiment being described, the material selected, namely silicon, has a negligible absorption. Accordingly, the plot of FIG. 2 used in the embodiment of the invention to be described is within energy region 22.

The reflectivity $R_2$ of interface 15 is conventionally determined by values of the respective refractive indexes between the two media, namely, the sapphire substrate 14 and the silicon layer 12, in the present embodiment. Accordingly, a comparison between measurements of the energy position of interference extrema, which determines the index of refraction of the material used, and the amplitude of oscillations that depend upon the reflection coefficient $R_2$ at the interface 15, can be used to make a determination of the crystalline quality of the interface 15. See O.S. Heavens, *Optical Properties of Thick Films*, Dovel Publishing, N.Y. 1965, pages 57–59 and pp. 156–158 for a description of these principles and the relationships between interference extrema position and amplitude of the reflection from the interface.

Figure 3:
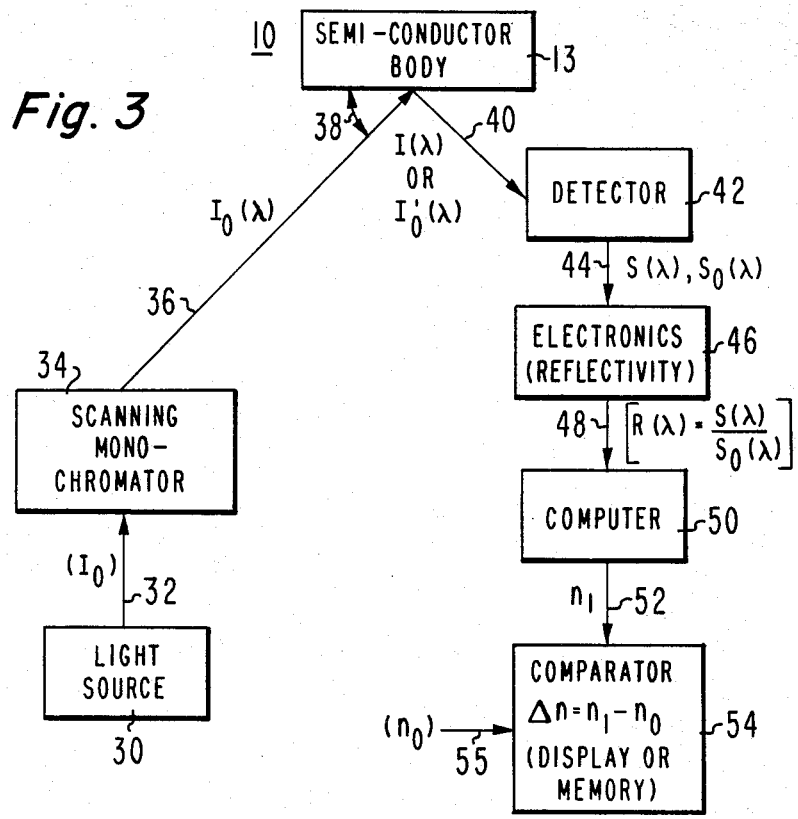
FIG. 3 is a block schematic of a system for making the measurements on the body of semiconductor material illustrated in FIG. 1 for determining the electronic properties thereof.

Before proceeding to a detailed description of the method of the invention, reference is now made to FIG. 3 illustrating a system for making the reflectivity measurements to determine the refractive index at the interface. A light source 30 of any suitable polychromatic light provides a light beam 32 having an intensity $I_0$ to a fast wavelength scanning monochromator 34. A suitable monochromator is a SPEX 14018, made by SPEX Industries, Metuchen, New Jersey. The scanning monochromator 34 provides a beam 36 of light intensity $I_0$ sequentially scanned rapidly at desired wavelengths $\lambda$. A scan in wavelengths between 0.5 to 1.0 micrometer is made to provide a continuous wavelength varying spectrum of light. In this spectral region wherein $\alpha d \ll 1$, the beam 36 illuminates the surface 13 of the semiconductor body 10 at an angle 38 that is nearly normal to the surface 13. The light is reflected as indicated by reflected beam 40 and directed to a photodetector 42 for converting the optical signal to an electrical signal. The electrical output signal of detector 42 is applied on path 44 to reflectivity electronics 46. Electronics 46 is a lock-in amplifier apparatus known in the art arranged to determine the amplitude of reflectivity as a function of wavelength $R(\lambda)$. A suitable amplifier is Model HR-8 manufactured by Princeton Applied Research of Princeton, New Jersey. Initially, the incident beam 36 is reflected from a mirror, not shown, to provide a calibration signal $I_0'(\lambda)$ to detector 42. This signal then provides the reference for the calibration of the system. Such a calibration signal is typically needed only once during a given set of measurements. For calibration purposes, detector 42 provides an electrical signal $S_0$ in amplitude equal to the intensity of optical signal $I_0'(\lambda)$. In operation, with the mirror removed, the incident beam 36 applied to the surface 13 of the body 10 will effect a reflected signal $I(\lambda)$. The reflected signal $I(\lambda)$ sensed by detector 42 provides a corresponding electrical signal $S(\lambda)$. Electronics 46 provides on path 48 to a computer 50, such as a microprocessor, the reflectivity signal $R(\lambda)$ which is equal to the ratio of the reflection intensity signal S and the reference intensity signal $S_0$. Computer 50 is programmed, as will be explained, to determine from the reflectivity signal (R) 17, the index of refraction $n_1$. A signal corresponding to the calculated index of refractivity ($n_1$) of the interface of semiconductor material 12 with the sapphire 14 is applied on path 55 to a comparator 54. Comparator 54 compares the calculated index of refraction $n_1$ with the known value of the index of refraction for the bulk silicon material. The difference of the two indicies is a measure of the crystalline quality of the silicon material at the interface 15. A suitable display or memory is included in the comparator 54.

Before proceeding to a description of the manner in which the quality of the interface 15 is determined, reference is made to the following relationships used in programing the computer 50 to make the calculations required.

The required intensity of the reflection coefficient $R_2$ as a function of wavelength can be derived from quantitative interpretation of the reflectivity (envelopes 18 and 20 of FIG. 2) test data. For a thin layer with negligible absorption ($\alpha d \ll 1$), the interference extrema of reflectivity may be represented by the following expressions:

$$R_{max} = \left( \frac{\sqrt{R_1} + \sqrt{R_2}}{1 + \sqrt{R_1 R_2}} \right)^2 \qquad (1)$$

$$R_{min} = \left( \frac{\sqrt{R_1} - \sqrt{R_2}}{1 - \sqrt{R_1 R_2}} \right)^2 \quad (2)$$

The maximum to minimum ratio of reflectivity from expression (1) and (2) is given by:

$$\frac{R_{max}}{R_{min}} = \frac{(\sqrt{R_1} + \sqrt{R_2})^2}{(1 + \sqrt{R_1 R_1})^2} \cdot \frac{(1 - \sqrt{R_1 R_1})^2}{(\sqrt{R_1} - \sqrt{R_2})^2} \quad (3)$$

Figure 4:
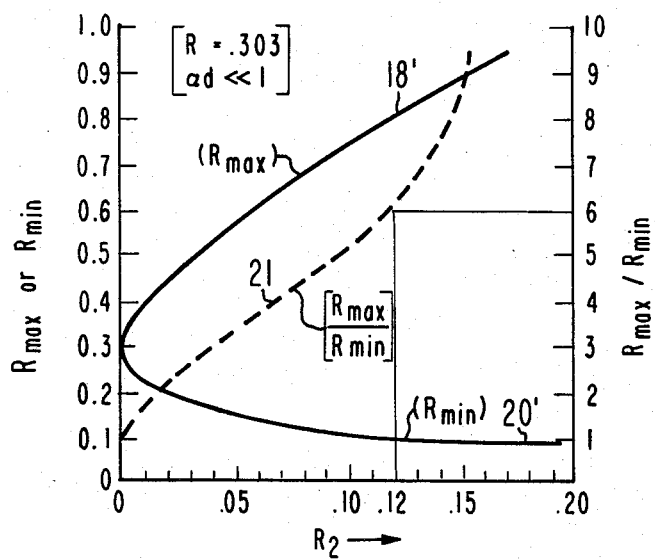
FIG. 4 are plots of the minima and maxima reflectivity as a function of the reflectivity ($R_2$) at or near the interface of the semiconductor body.

Calculated values of $R_{max}$, $R_{min}$ and $R_{max}/R_{min}$ as a function of $R_2$ are shown in FIG. 4 for $R_1$=constant and $a_d \ll 1$. It is seen that $R_{max}$ and $R_{max}/R_{min}$ increase with increasing values of the interface reflectivity $R_2$.

As explained above, since the material of silicon in the present embodiment has negligible absorption, equation (3) is used to perform the calculations.

A plot of the envelope curves 18 and 20 of FIG. 2 are shown in FIG. 4 as curves 18' and 20' as a function of the reflectivity ($R_2$) at the interface 15. The reflectivity $R_2$ is calculated from equation (3) assuming a known value of $R_1$, namely the reflectivity of 0.303 at the surface 13 of silicon and the value of $R_{max}/R_{min}$ is derived from the measurements with the apparatus of FIG. 3. The ratio of the extrema is determined by computer 50 suitably programmed to respond to the reflectivity signals on path 48 to generate the envelope curves 18' and 20' from which the ratio of the extrema represented by curve plot 21 in FIG. 4 is provided. With such a curve 21 it can be seen that for any given ratio of the extrema, the reflectivity $R_2$ from the interface 15 can be graphically determined. Thus, a ratio, say an extrema ratio of 6 (right ordinate of FIG. 4) shows a reflectivity $R_2$ of about 0.12.

The index of refraction $n_1$ of the interface material is calculated from the well-known relationship of the reflection coefficient and the respective indexes of refraction between two media as follows:

$$R_2 = \left( \frac{n_1 - n_2}{n_1 + n_2} \right)^2 \quad (4)$$

where $n_2$ is the index of refraction of the second medium, namely sapphire, used in the insulator portion 14 of the SOS body 10; and $n_1$ is the index of refraction of the interface 15.

In operation, the apparatus of FIG. 3 is used to determine the index of refraction $n_1$ and ultimately, give an indication of the quality of the material of the interface as follows:

The light beam 36 is applied to the semiconductor body 10, after calibration, to provide via detector 42 and electronics 46 a reflection signal $R(\lambda)$ on path 48 which is applied to the computer 50. Computer 50 calculates in sequential steps:

(1) the envelope 18 and 20 of the extrema of the reflectivity signal (R) 17 oscillations effected by the optical interference between interface 15 and the surface 13 of body 10 from which the reflected signal $I(\lambda)$ was applied to the detector 42, etc.;

(2) the ratio of the extrema ($R_{max}/R_{min}$) represented as curve 21 in FIG. 4;

(3) equation (3) is now used to calculate reflectivity $R_2$ (from surface 15) based on the tested values of the extrema (curve 21) and the known value of the reflectivity R at surface 15, namely 0.303;

(4) equation (4) is then solved for the refractive index $n_1$ using the value of the reflectivity $R_2$ determined from the calculation of equation (3) and the known value of the index of refraction $n_2$ of sapphire. It should be appreciated that the index of refraction of a material will change as a function of the wavelength of the incident light, and, accordingly, as a function of the incident photon energy (E) in electron volts (eV). The calculated value of the index of refraction $n_1$ is converted to a signal and applied via path 52 from the computer to comparator 54. This index of refraction $n_1$ we have discovered, as stated above, is different from the index of refraction $n_0$ of the bulk silicon material in layer 12. Evidence of this difference will be explained in detail hereinafter.

In order to provide an indication of the quality of the crystalline silicon at the interface 15, we provide a signal on path 55 representing the index of refraction $n_0$ of the silicon. Accordingly, the comparator 54 compares the two indicies ($n_1$ and $n_0$) to provide a number which manifests the quality of the crystalline silicon at the interface 15.

A tabulation of a number of tests made in accordance with the invention are provided below. The data is based on eight SOS layer samples which were different in the following respects: Samples 1, 2, 5 and 7 are "as-grown" silicon having different crystalline quality as determined by UV reflectometer techniques, as described in the above-identified U.S. Pat. No. 4,352,017. From such tests, samples 1 and 2 were shown to be the best quality. Samples 5 through 8 were shown to be good but of lesser quality; while samples 3 and 4 were the poorest quality. Samples 4 and 6 were hydrogenated while sample 8 was heat treated. As was hereinabove explained, the method of the invention is based on the principle that there is no measurable difference in the refractive index $n_0$ in such varied forms of silicon.

TABLE 1

| | Theoretical Limits | | $R_2$ (Test Data for SOS Samples) | | | | | | | |
|---|---|---|---|---|---|---|---|---|---|---|
| | Limit* | Limit** | 1 | 2 | 3 | 4 | 5 | 6 | 7 | 8 |
| $\frac{R_{max}}{R_{min}}$ (1 eV) | 5.34 | 6.3 | 6.1 | 6.1 | 6.1 | 6.0 | 6.3 | 6.1 | 6.3 | 5.9 |
| $\frac{R_{max}}{R_{min}}$ (1.8 eV) | 5.37 | 9.5 | 6.5 | 6.5 | 7.0 | 6.3 | 6.7 | 6.3 | 7.7 | 6.3 |

In the table, the "theoretical limits" are used as a comparison for the extrema values determined by the tests and subsequent calculations of the SOS samples. The theoretical limit* was calculated by using the refractive index of bulk crystalline silicon on sapphire while the limit** was calculated using reflectivity $R_1$ for silicon and reflectivity $R_2$ for amorphous silicon on sapphire. A study of the Table for the samples tested shows that the closeness of the values of $R_2$ to the value of the limit* is an indication of the closeness in crystalline quality of the sample to the crystalline quality of the bulk material. It is seen also that for high photon energy light, at, for example, 1.8 eV, the value of 7.7 for sample 7, is quite high and close to the limit** of amorphous silicon. The quality of such a sample is relatively poor whereas a value of 6.3 for sample 4, is relatively better.

The method of the invention being described was carried out using many samples of hetero-epitaxial silicon-on-sapphire wafers of 3-inch (7.5 centimeter) diameter. SOS wafers often exhibit silicon film variations which exceed ±5%. In order to reduce, if not minimize, the error resulting from thickness variations, it is preferred that the diameter of an incident beam (beam 36, FIG. 3) be about 1 mm. SOS wafers contain a rather homogeneous central portion and a highly inhomogeneous peripheral region (within 1 cm from the wafer edges) which is of inferior crystalline quality. The data of the table above was based only on the central portions of the wafers tested.

As indicated above, the present method depends on the fact that the refractive index ($n_0$) of the bulk material of a semiconductor is independent of the processing history of the material. The crystalline quality of the interface material is manifested by the difference between the measured value $n_1$ and the actual value $n_0$ of the bulk material.

Figure 5:
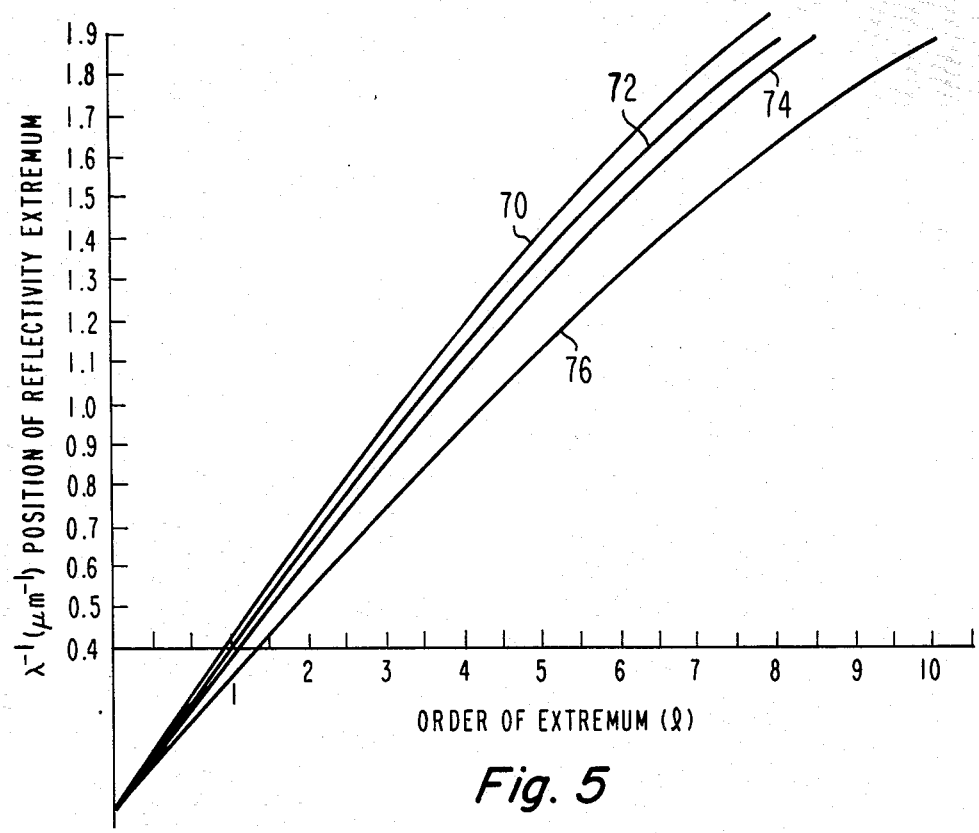
FIG. 5 are plots of the position of the reflectivity extrema and the wavelength reciprocal at each position.
Figure 6:
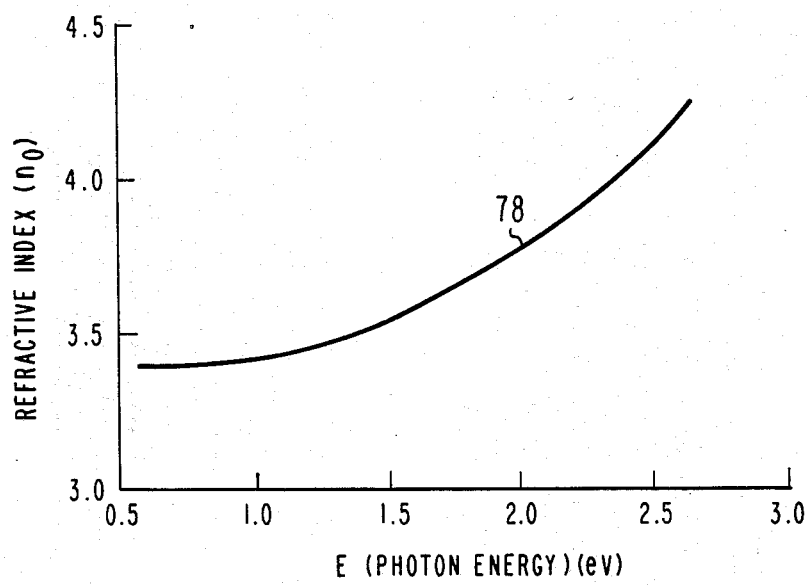
FIG. 6 is a plot of refractive index as a function of photon energy dispersion or reciprocal of wavelengths for samples of SOS films.

The refractive index ($n_1$) of the silicon material at interface 15 is determined indirectly by calculation from the measured reflectivity extrema data (curves 18 and 20). The substantiation of the process of the invention will be understood by first referring to FIG. 5. A consecutive number of reflectivity minima, such as minimum 60, shown in FIG. 3 are plotted for each sample as a function of the respective reciprocal of wavelength ($\lambda^{-1}$) at each minimum. The plots shown in FIG. 5 are for six tested samples. The sample included those that are (1) as-grown silicon, (2) hydrogenated silicon, and (3) heat-treated silicon. The extrema are determined by computer 50 responding to the tested reflectivity signal $R(\lambda)$. Computer 50 is programmed to calculate the reciprocal wavelength position from the relation:

$$l \cdot \lambda_l = 2\, d n_0(\lambda) \qquad (5)$$

where l is the consecutive order of extremum (point 60, for example in FIG. 2), d is the thickness of the semiconductor layer, $n_0$, is the index of refraction of the bulk silicon 12, and $\lambda_l$ is the wavelength at each of the extremum. The four plotted curves 70, 72, 74 and 76 shown in FIG. 5 indicate the average of the tested samples. The corresponding photon energy relation to wavelength is:

$$E_l(eV) = 1.24/\lambda_l\,(\mu m) \qquad (6)$$

where $E_l$ is the photon energy in electron volts (eV) and 1.24 is the well-known conversion factor of wavelength to photon energy. Equation (5) and (6) were used to plot curve 78 shown in FIG. 6. Curve 78 is the value of $n_0$ obtained from curves 70, 72, 74 and 76 of FIG. 5. Curve 78 shows the refractive index $n_0$ as a function of the incident photon energy. Note that curve 78 represents the composite data from each of the tested samples. This result shows that there is no measurable difference in the value of bulk refractive index $n_0$ between the various samples, whether the films thereon were (1) as-grown, (2) hydrogenated or (3) heat-treated. Because of the same value of $n_0$ among the different specimens we are assured that the observed differences in the relativity curve 17 (FIG. 2) are related to the interfacial index of refraction $n_1$.

What is claimed is:

1. A method for determining the crystalline quality of one material at an interface between said one material and a different material of different crystalline lattice, said one material (1) having an exposed surface opposed to said interface, (2) having negligible absorption in a given optical spectrum, and (3) having a known reflection coefficient at said exposed surface, comprising the steps of;
   (a) exposing said exposed surface to a light beam scanned sequentially with wavelengths within said optical spectrum whereby light reflected from said exposed surface oscillates in intensity between extrema as a result of interference reflections between said exposed surface and said interface;
   (b) measuring the intensity of reflections from said surface at each respective wavelength to obtain a series of reflection intensity signals corresponding to each said wavelength;
   (c) determining from said reflection signals said reflectivity extrema;
   (d) determining from said extrema the refractive index of said one material at said interface, said refractive index being a measure of the crystalline quality of said one material at or near said interface and comparing the bulk index of refraction of said one material to said determined index of refraction of said one material at or near said interface, the difference between said respective indexes being a measure of the quality of said one material at said interface.

2. The method of claim 1 comprising the step of selecting said one material to be essentially monocrystalline silicon and said different material to be sapphire.

3. The method according to claim 1 comprising the step of selecting the value of said optical spectrum of light to have a value within the range of 0.5 to 1.0 micrometer.

4. The method according to claim 1 comprising the step of selecting the thickness of said one material to have a value on the order of 0.5 to 1.0 micrometer.

* * * * *